United States Patent [19]
Smith

[11] Patent Number: 5,654,415
[45] Date of Patent: Aug. 5, 1997

[54] ANTISENSE OLIGONUCLEOTIDES TO P53

[75] Inventor: Larry James Smith, Omaha, Nebr.

[73] Assignee: University of Nebraska Board of Regents, Omaha, Nebr.

[21] Appl. No.: 327,371

[22] Filed: Oct. 21, 1994

Related U.S. Application Data

[62] Division of Ser. No. 748,997, Aug. 23, 1991, abandoned.

[51] Int. Cl.$^6$ .......................... C07H 21/04; C12N 15/00
[52] U.S. Cl. ............................ 536/24.5; 935/34; 935/36
[58] Field of Search ........................ 536/24.5; 514/44; 935/34, 36

[56] References Cited

PUBLICATIONS vander Krol et al (1988) Biotechniques 6, 958–976.
Tseng et al (1994) Cancer Gene Therapy 1, 65–71.
Harlow et al (1985) Molec. Cell. Biol. 5, 1601–1610.
Tuck et al (1989) Molec. Cell Biol. 9, 2163–2172.
Zon (1988) Pharm. Res. 5, 539–549.
Sambrook et al (1989) Molecular Cloning, Cold Spring Harbor Laboratory Press, Cold Spring Harbor, NY, pp. 14.5 and 14.15.
James (1991) Antiviral Chem & Chemother. 2, 191–214.

*Primary Examiner*—Jasemine C. Chambers
*Assistant Examiner*—Deborah Crouch
*Attorney, Agent, or Firm*—Dann, Dorfman, Herrell and Skillman

[57] ABSTRACT

Antisense oligonucleotides and composition of oligonucleotides are taught which inhibit the proliferation of cells without affecting cell viability. p53 antisense oligonucleotides are shown to inhibit the proliferation of tissue culture cells expressing this gene. Methods of treating a patient with such antisense oligonucleotides is described.

3 Claims, 1 Drawing Sheet

5,654,415

ANTISENSE OLIGONUCLEOTIDES TO P53

This is a division of application Ser. No. 07/748,997, filed Aug. 23, 1991 now abandoned.

BACKGROUND OF THE INVENTION

1. Field of the Invention

The present invention relates to methods and compositions useful in treating disorders in which the direct cause of the clinical disorder is the expression in the primary diseased cells of a differentiation program that does not normally exist. Such disorders are hereinafter referred to as Aberrant Programming (AP) Diseases. The invention also relates to method and compositions useful in therapeutically reprogramming normal cells.

As will be discussed more fully hereinafter, the AP diseases of this invention constitute a new disease classification and there is presented a novel molecular model of pathogenesis for these diseases. According to the molecular model of this invention, the basic disease causing entity in the AP diseases is a specific type of relational alteration among certain cellular Components involved in program control. It is unlike any previously described molecular pathogenic mechanism. This model defines the nature of the therapy for these diseases, limits the potential set of therapeutically useful targets to a relatively small number of genes and leads to the unobvious conclusion that this includes the manipulation of certain "normal" genes is an appropriate approach for the treatment of AP diseases, thus, leading to a unique approach to therapy for the AP diseases of this invention. This model makes the selection of targets for proposed therapy straightforward and accessible to anyone skilled in the art.

A preferred embodiment relates to the reprogramming of cell behavior through the manipulation of transcriptional regulators (TRs). The invention includes systemic treatment and compositions for such treatment, as well as in vitro manipulation of cells prior to transplantation of such cells with the host under treatment.

2. Description of the Related Art

Very recent studies involving the use of antisense oligonucleotides for treatment of cancer have been reviewed by Stein and Cohen, Cancer Res. 48:2659 (1988). Several types of antisense molecules have been screened for their ability to inhibit the synthesis of particular proteins using both intact cells and in vitro systems for protein synthesis (See Ld. and Paoletti, Anti-Cancer Drug Design 2:325, 1988). For example, agents with specificity for RNA transcribed from the myc gene have been reported to inhibit the proliferation of the human AML line HL60 (Wickstrom, et al., Proc. Natl. Acad. Sci. USA 85:1028 (1988) and normal T lymphocytes (Heikkila, et al., Nature 328:445 (1987), and oligodeoxynucleotides complementary to cyclin mRNA have been reported to suppress the division of 3T3 cells (Jaskulski, et al. 1988).

More recently, it has been found that in the treatment of cancer with ODNs against myb, the proliferation of leukemic cells was inhibited with an accompanying lower degree of inhibition against normal cells. (Calabretta et al, PNAS, 88, 2351, 1991.) Also, it has been shown that transient inhibition in a leukemia cell line resulted with an ODN against myc; however, unfortunately, a comparable inhibition against normal cells occurred (Zon et al patent). This patent also discloses inhibition of HIV replication using ODNs targeted to viral genes. Belenska et al (Science, 250, 997, 1990) have proposed the use of double stranded ODNs, binding to TR ligands as potential therapeutic agents for disease causing genes. They give blocking of NF-kB binding to HIV enhancer as an example. The use of retroviral vectors carrying antisense oncogenes for the treatment of cancer is known.

The fundamental problem with the foregoing art is that it is based on the notion that the expression of specific molecular abnormalities (altered regulation or mutation of endogenous genes or expression of exogenous genes) in the disease cells of these patients directly cause the clinical pathological features of the AP disease. It follows from such thinking that the therapeutic strategies should be directed to attacking these molecular abnormalities.

In the case of cancer, contemplated therapy involving antisense expression vector ODNs have been directed to oncogenes in accordance with the oncogene/anti-oncogene cancer model, or to growth factors expressed by cancer cells in accordance with the autocrine model. In the case of AIDS therapeutic strategies involving such agents being developed are directed toward blocking HIV expression and/or infection. There are no counterpart causal agents identified to the other AP diseases. Hence the therapeutic approaches under development are more empirical.

According to the AP disease model the fundamental pathology causing the clinical pathological features of these disorders is both relational and dynamic. In stark contrast to the prior art, the therapy of the present invention involves manipulation of patterns of TR expression. The invention provides an entirely new approach to the treatment of said selected diseases and provides a rational, empirical basis for the design of novel agents. The therapeutic reprogramming of normal tissue involving ODNs is unprecedented.

SUMMARY OF THE INVENTION

In accordance with this invention, there is provided a method for reprogramming cell behavior to achieve therapeutic effects through manipulating patterns of TR expression.

Also provided is a method for treating an individual having an AP disease comprising administering to said individual an effective amount of a composition selected from the group consisting of an expression vector, a double stranded ODN, and an antisense ODN. Said composition must be capable of regulating expression of a TR. Said TR is expressed by the AP cells and further characterized by the fact that it exhibits a therapeutically useful change in said cell behavior in the Reprogramming Test of this invention (hereinafter more fully described). It is noted that when the AP disease is AIDS, said TR is not encoded by HIV. In the case of cancer, said TR is a Traitor Gene of this invention (more fully discussed hereinafter) and, preferably, excludes oncogenes, e.g. fos, myc, myb, rel, jun (in an altered form).

Another embodiment of this invention is a method for treating an individual having a clinical disorder comprising administering to said individual an effective amount of a composition selected from the group consisting of a double stranded ODN and an antisense ODN. The composition is capable of regulating expression of a TR. The TR is expressed by therapeutically relevant cells and is further characterized by exhibition of a therapeutically useful change in said cell behavior in the Reprogramming Test of this invention.

The invention revealed here primarily embodies a new type of therapy based on reprogramming cellular behavior. Collateral inventions, however, also follow including: (1) the diagnosis and/or staging of aberrant programming diseases by assaying for the expression of particular transcriptional regulators and their variants in diseased cells; and, (2) for any given aberrant program disease, the use of test agents in vitro for determining the optimum agent(s) for treating any particular patient.

Thus, there is provided a method for diagnosing or staging an AP disease comprising identifying the relevant subset of TRs expressed by AP cells from an AP patient. A method for selecting the most efficacious treatment regimen for an AP disease forms another embodiment. This embodiment comprises identifying the relevant subset of TRs expressed by AP cells from an AP patient. These embodiments are described more fully hereinafter.

In addition, the invention provides a method for treating therapeutically relevant cells from an individual having a clinical disorder prior to transplantation of the cells back into the individual (autologous transplant) embodiment. This embodiment comprises the steps of:
a) obtaining therapeutically relevant cells from the individual and
b) exposing the therapeutically relevant cells to a reprogramming amount of an ODN having a sequence complementary to a sequence of RNA transcribed from a TR regulated gene or double stranded ODN ligand of a transcriptional regulator present in the TR cells. In a preferred embodiment the cells are taken from prenatal tissue or from a different donor than the individual under treatment (allogeneic transplant).

Selection of the most efficacious treatment regimen for an AP disease forms another embodiment of this invention. This method involves removing and culturing AP disease cells from an AP disease patient with an antisense ODN specific to a TR from the relevant subset of TRs expressed by AP cells from an AP patient or a double stranded ODN to the DNA binding domain of such TR to determine optimal treatment.

In carrying out the methods of treating AP diseases of this invention it is critical to select the proper targets. Hence, an important embodiment of this invention is a method for the selection of a target for the treatment of an AP disease comprising (i) determining the subset of transcriptional regulators and their direct modifiers expressed by the aberrantly programmed tissue, the corresponding normal tissue, or the constitutively self-renewing normal tissue or, alternatively, making a similar determination for any other normal tissue that is to be therapeutically manipulated in accordance with this invention; (ii) adding or subtracting expression of transcriptional regulator(s), or their direct modifiers, from cells to be therapeutically reprogrammed and the appropriate control tissue; (iii) scoring effect on cellular programming and selecting potential therapeutic agents according to the Reprogramming Test; (iv) testing effect of addition or subtraction of the function of particular transcriptional regulators, using the agents selected, (in an animal model system if the therapeutic agents are for systemic use), and (v) reducing or eliminating any undesirable side effects that might be produced by the potential therapeutic agents. This embodiment is described in detail hereinafter.

Exploiting specific cell type differences in target RNA for selecting differentially available sites for ODN binding forms another embodiment of this invention. This embodiment comprises a method for cell type dependant targeting of specific RNA transcripts comprising selecting an ODN capable of binding to and leading to the destruction of said RNA in the tissue to be therapeutically manipulated, but not in tissue where side effects are produced by destruction of said RNA. Exemplary is the use of an antisense ODN directed to cyclooxygenase RNA that selectively binds to and destroys said RNA in hematopoietic tissue while avoiding said RNA in gastrointestinal tissue.

All of the foregoing embodiments involve reprogramming of cell behavior to achieve therapeutic effects through manipulating patterns of TR expression.

DESCRIPTION OF THE PREFERRED EMBODIMENTS

AP Disease Model and List

Definition of a "cellular program"

Figure 1:
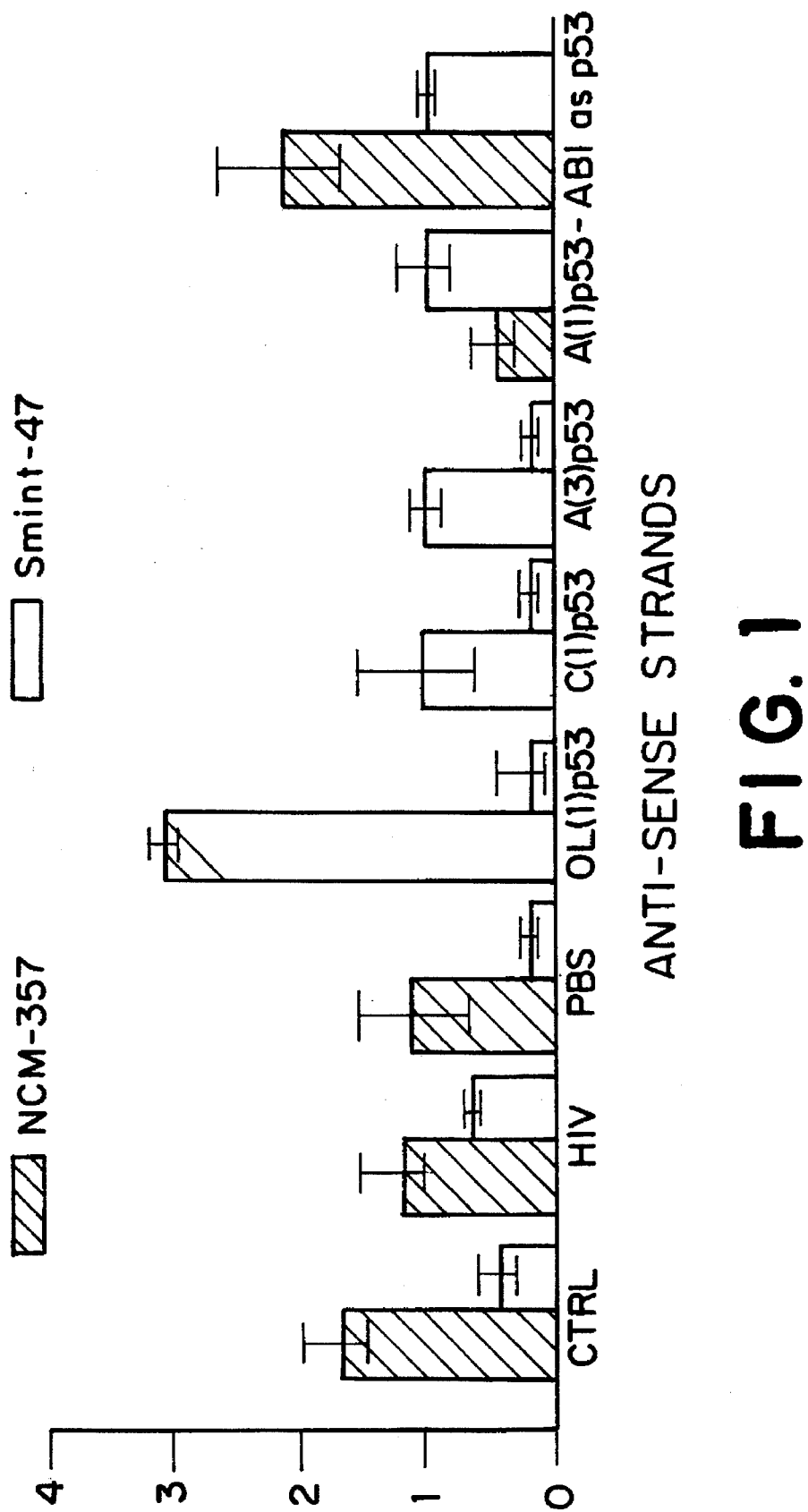
FIG. 1 two primary normal human cell types were used in this study; NCM357 (colon mucosa) and SMINT-47 (fetal small intestine). Cells were initially grown in T-57 flasks in M3;2 medium as previously described (see table III). The cells were seeded in 96-well plates and six different oligonucleotides were added to give 10 micromolar concentrations. On day ten representative cultures were harvested and a thymidine incorporation assay performed. The results form the viability and total cell counts indicated no decrease in cell viability. The remaining cultures were placed in medium free of oligonucleotides. These all returned to normal growth indicating that any effects produced by the oligonucleotides was reversible.

The coordinated appearance in cells of a cell type restricted pattern of gene expression over time that provides for a particular phenotype and as a result for the determination of the range of possible cellular responses to exogenous stimuli.

The fundamental program can be thought of as a differentiation program which in turn controls the subprogram responses of the cell to environmental and other exogenous cues where the subprograms include cellular viability (apoptosis) and proliferation.

Definition of an "Aberrant Programming Disease"

One in which the direct cause of the clinical disorder is the expression in the primary diseased cells of a differentiation program that does not normally exist. That is, there is an expression of normal genes that provide for particular differentiated phenotype in abnormal combinations. The result is that these diseased cells become capable of expressing pathogenic behaviors involving cellular differentiation, viability and proliferation. These attributes of the primary diseased cells can also induce pathologic change, in their tissue environment.

The term "direct cause" with respect to pathogenesis is to be distinguished from "risk factors." Typically an AP Disease will be associated with numerous risk factors that in various combinations appear to "cause" the appearance of the disease. In fact, however, they cause the changes in the pattern of transcription regulator (TR) expression and chromatin domain availability which in turn causes the disease. This is important because programs can evolve and can become independent of any risk factors involved in their induction. Risk factors include mutagenic events, viruses, chromosomal abnormalities, genetic inheritance, and diet.

Aberrant programming disorders can be manifested as either a hyperplastic or a hypoplastic (degenerative) disease or a combination of both.

Examples of diseases where the aberrant program phenotype is expressed:
Cancer
Myeloproliferative Diseases
polycythemia vera
agnogenic myeloid metaplasia essential thrombocytosis
Myelodysplasias
refractory anemia
refractory anemia with ringed sideroblasts
refractory anemia with excess blasts
refractory anemia with excess blasts in transition
Atherosclerosis
AIDS-related complex
AIDS

Molecular Model

According to the molecular model set forth herein, the basic disease causing entity in the AP diseases is a specific type of relational alteration among certain cellular components involved in program control. It is unlike any previously described molecular pathogenic mechanism. This model defines the nature of a novel therapy for these diseases, limits the potential set of therapeutically useful targets to a relatively small number of genes and leads to the unobvious conclusion that the manipulation of certain "normal" genes is an appropriate approach for the treatment of AP diseases, in this way the model makes the reduction to practice of the proposed therapy straightforward and accessible to anyone skilled in the art.

Specifically, the essential molecular pathology in the AP diseases consists of changes in the interdependent patterns of TR expression and/or chromatin domain availability for transcription. In turn, these relational alterations provide for the expression of abnormal cellular programs involving cellular differentiation which are pathogenic. Particular TR or certain molecules involved with the control of domain status may be structurally abnormal. However, these are not necessarily useful targets for therapeutic intervention.

Tenets of the model relevant to the development of specific therapy:

A) Those true of both normal and aberrant programming:
1) The pattern of domain availability determines the possible range of genes that can be expressed in the cell and, therefore, limits the range of cellular programs that can be expressed.
2) The pattern of TR expression is the molecular equivalent of a programming code. By analogy with language particular combinations of TR (letters) working as a unit (words) regulate the expression of sets of genes in a coordinate fashion while the complete set of TR combinations used in any given cell (sentence) determines which of the possible phenotypes the cell will expressed, and therefore the overall character of the cell's differentiation program (see Table I for more details where cancer is used as an example).
3) Only a subset of the total number of TRs involved in the control of cellular differentiation for the total organism are expressed in any given cell type and they are few in number.
4) Similar effects on particular patterns of gene expression (programming) can be achieved by more than one specific combination of TR (synonyms).
5) The specific functional consequences of a particular TR's being expressed is context-dependent. That is, its effects on cellular programming depends both on which other TR it combines to regulate a particular set of genes (what words it appears in) and on the total set of different TR combination expressed by the cell (the sentence).

B) True of AP cells but not normal cells:
1) The combinations of TR seen in AP cells is different from that seen in any normal cell (the sentence is not expressed by any normal cell).
2) The specific functional consequences of any given particular TR being expressed in an AP cell, therefore, will be different from the consequences seen in a normal cell.
3) AP cells, therefore, express a cellular differentiation program that is different from any normal differentiation program. As a result AP cells express pathogenic behaviors resulting from their altered differentiation, viability and proliferation characteristics.
4) Hence, equivalent manipulations of the expression of a given TR in normal cells vs. aberrantly programmed cells can produce differential effects on cellular behavior. This can form the basis of therapeutic intervention.
5) The subset of TRs expressed by any AP cell is expected to include TR not expressed by the corresponding normal cells and/or conversely. These TRs within the AP cells will be normal TRs ectopically expressed or modified (alternate splicing promoter use or post-translational modification) or mutated to a TR with altered binding properties.

Nature of Targets

TRs are the primary targets for therapeutic manipulations based on the model. They may be manipulated directly or indirectly through molecules such as tyrosine kinase, that can effectively change a TR of one type to another through structural alterations such as phosphorylation.

Nature of Therapeutic Intervention

The basis of the novel therapy is to differentially change the pattern of gene expression in AP cells by altering the pattern of TR expression. The model states that the specific functional consequences of the expression of any given TR is context-dependent. It therefore follows that the same TR present in both normal and AP cells can be manipulated in the same way and a different impact on cellular behavior obtained.

A TR expressed only by the AP cells, however, also may be targeted. The end result is that the pattern of gene expression in the AP cells lose at least a substantial portion of their disease-producing activity. This can be manifested in numerous possible ways including death of the AP cells, a change in their differentiation status with a concomitant change in the production of disease-producing factors or to a loss of proliferative potential.

The number of transcriptional regulators that will have to be manipulated in any given cell type will be very small. There are estimated to be 30,000 to 100,000 genes in the human genome distributed over $3 \times 10^9$ bp of DNA. In any given cell type approximately 10,000 genes can be shown to be expressed. Greater than 90% of these are expressed by many cell types and the large majority of these are referred to as "housekeeping genes."

Typically, the number of genes that can be shown to be differentially expressed in any given cell type account for only a few hundred. It is these genes that make the difference between liver cells and brain cells, for example. The large majority of these are directly involved in carrying out the functions that characterize the cell type. Liver cells, for example, express a wide range of enzymes that are involved in ridding the body of many types of chemicals. The genes of interest for the purposes of this patent are the small subset of genes coding for molecules involved in the differential regulation of cell type specific genes. In particular, transcriptional regulators and their direct modulators. The latter includes, for example, certain tyrosine kinases, that can modify a particular transcriptional regulator and, in effect, change it to a functionally different transcriptional regulator. (Berk Biochem Biophys. Actn. 1009, 103, 1989) For the purposes of this invention transcriptional regulators are defined as molecules that bind to specific DNA sequences variably expressed by different genes and/or to other transcriptional regulators at least one of which must bind to specific DNA sequences. As a result they control the levels of gene expressions by means of modulating RNA polymerase activity. The transcriptional regulators may be of either endogenous or exogenous origin. They may either be normal or be mutated.

The ability of transcriptional regulators to variably interact with each other provides the basis for a combinational regulatory system. This allows a very small number of transcriptional regulators to control the expression of a large number of genes in various patterns. Particular sets of genes being controlled at any given time by a certain subset of the transcriptional regulators being expressed by the cell. Each transcriptional regulator subset, therefore, is a programming code or an instruction or a "word" that directs the expression of a particular gene set. The entire pattern of gene expression being expressed by a given cell type can be thought of as a sentence, since only certain words can appear together.

A general role for combinatorial regulation being involved in eukaryotic gene expression has been previously postulated by several investigators. (Scherrer, and Marcand J. Cell Phys 72, 181, 1968; Sherrer Adv. Esp. Med. Biol. 44, 169, 1924; Gierer Cold Spring Harbor Symp Quant Biol 38; 951, 1973; Stubblefield J. Theor Biol 118, 129, 1986, Bodnar J. Theor Biol 132, 479, 1988) Lin and Riggs (Cell 4, 107, 1975), demonstrated using biophysical arguments the impossibility of having a separate regulator for every gene in a eukaryotic cell. Combinatorial regulation models of eukaryotic gene expression generally postulate multiple levels of regulation in addition to transcription. In principle, these models show how theoretically 100,000 genes could be selectively controlled by as few as 50 regulatory molecules only a small subset of which would operate at the level of what is defined here as transcriptional regulators. Bodnar J. Theor. Biol. 132, 479, 1988.

The actual number of human transcriptional regulators are estimated to number on the order of somewhere in excess of 100. (Table II lists those that have been described in the literature.) Many, however, are known to be expressed only in certain cell types. Since just a few hundred genes determine the differences between particular differentiated cell types and the large majority of these determine the particular functional features of the cell, only a very small number of these can be regulator gene products.

It follows, therefore, that the number of regulators that must be manipulated to achieve the effects stipulated by this invention for any given application is small and can be managed with comparatively modest effort. It also follows from the notion of combinatorial regulation that not all the transcriptional regulators expressed by a given cell type need to be known before this invention can be practiced.

The present inventor has found that antisense p53 oligonucleotides can inhibit the proliferation, including the blocking of stem cell self-renewal, and ultimately kill primary human leukemic blasts while not producing similar effects on fresh normal bone marrow cells. This unobvious result indicates that the interactive mechanisms for detecting, interpreting and responding to environmental informational molecules involved in regulating cell differentiation and proliferation and viability in AP cells are so altered from normal in terms of their dynamic interactions (involving signal transduction and interpretation) that the inhibition of a single gene or set of genes coding for proteins involved in this process by antisense oligonucleotides is sufficient to change the impact of the informational molecules so a change in cellular programming such as cellular death or growth inhibition program can be selectively instituted in AP cells. The term "traitor genes" is used herein to describe those genes in AP cells that may be suitable for targeting for inhibition with antisense molecules in accordance with the present invention Suitable target or traitor genes may themselves either be functionally abnormal or be normal but function to maintain the pathological phenotype AP cells as part of an abnormal pattern of gene expression. Such treatment results in differential programming of AP cells, but not their normal counterparts over a selected dose range. In the preferred embodiment the Traitor Genes to be targeted are TRs.

The concentration of oligonucleotide to be used may vary, depending upon a number of factors, including the type of cancerous cells present in the marrow, the type, and the specificity of the particular antisense oligonucleotide(s) selected, and the relative toxicity of the oligonucleotide for normal cells. Although the present inventor has observed significant AP cell programming at oligonucleotide concentrations in extra-cellular fluid as low as 1 nanomolar, optimal inhibition was observed at concentrations of at least 10 nanomolar in the model system described below. The upper limit of the dosage range is dictated by toxicity and therapeutic efficacy, and, generally will not exceed 5 micromolar. With the aid of the techniques set forth in the present disclosure, those of skill in the art should be able to determine the optimal concentration to be used in a given case.

"Hardware" for Reduction to Practice

Using established techniques, assays and agents, the following capabilities can be readily acquired. These can be used by anyone skilled in the art to reduce the primary and collateral inventions to practice.

1) Assays for transcriptional regulators and their direct modifiers.
Preferred assays: RNA in situ hybridization (Lum Biotech. 4, 32, 1986) or PCR (Block, Biochem 30, 2735, 1991) or metabolic labelling (Ausubel et al (eds.) Current Protocols in Molecular Biology, John Wiley N.Y., 1989 (updated semiannually)) for detecting expression at the protein level.

Purposes:

To establish the subset of the known transcriptional regulators or their direct modifiers that are expressed by a particular cell type. This will serve the following functions:
a) the determination of the subset of transcriptional regulators, or their direct modifiers, that are targets to be manipulated in the reduction to practice;
b) the evaluation of the effectiveness of potential therapeutic agents in adding or subtracting the expression of a particular transcriptional regulator or its direct modifier cells;
c) the diagnosis and/or staging of a particular aberrant program disease;
d) the determination of the optimum therapeutic agent(s) in clinical practice, when there are more than one option for a given disease.

2) Agents for adding or subtracting the expression of particular transcriptional regulators or their direct modifiers in cells to be therapeutically manipulated.

a) Antisense oligonucleotides (Zon, Pharmaceut. Res., 5, 539, 1988).

These agents can be used to subtract the expression of particular genes from cells.

Design of "test" antisense oligonucleotides i) Using a computer program such as "Oligo" (Rychik and Rhoads, Nucl. Acids Res., 17., 8543, 1989) select a set of antisense oligonucleotides that bind to the RNA target of choice that have the following characteristics: (1). length between 10 and 35 bases with 20 being generally used; (2) negligible self-interaction (self-dimers and hair pins) under physiologic conditions; (3) melting temperature $\geq 40°$ C. under physiological conditions; and (4) no more than 40% of the oligonucleotide being a run of guanines or cytosines);

ii) Using a reference such as Genbank ensure that the antisense oligonucleotide has $\leq 85\%$ homology with the RNA transcripts of other genes. An exception to this is where an antisense oligonucleotide is selected on the basis of its ability to bind to more than one member of a transcriptional regulator family (such as the homeobox genes) on the basis of sequence homology.

b) Establishment of "prototype therapeutic" antisense oligonucleotide from a set of test antisense oligonucleotides. These prototype compounds will be used in the reduction to practice.

i) Synthesize test antisense oligonucleotides using standard procedures, for example, those for producing phosphorothioates (Vu et al, Tetrahedron Lett, 32, 3005, 1991).

ii) Using assays for transcriptional regulators or their direct modifiers select prototype therapeutic antisense oligonucleotides out of the set of test compounds on the basis of shutting down expression of the target gene in the cell types to be therapeutically manipulated. In practice, the same set of prototype agents capable of shutting down target gene expression in a variety of cell types could be used in the Reduction to Practice, Step 2, hereinafter, for multiple therapeutic objectives.

b) Synthetic double-stranded oligonucleotides that are ligands for the DNA binding domain of one or more transcriptional regulators. (Wu et al, Gene, 89, 203, 1990)

Prototype therapeutic agents of this type for use in the reduction to practice will correspond to actual gene sequences to which the transcriptional regulator(s) will have been shown to bind using standard techniques such as the gel mobility shift assay. (Ausubel et al (eds.) Current Protocols in Molecular Biology, John Wiley N.Y., 1989 (updated semiannually).)

c) Expression vectors

In the preferred embodiment a recombinant viral vector will be used (Miller and Rosman, Biotech, 7, 980, 1989) that carries the complete coding sequence of the transcriptional regulator or its direct modifier. This will provide for expression of the regulator or modifier in the cells of interest. It will be constructed and tested using standard methods. (Ausubel et al, supra) Alternatively, the viral vector will carry a sufficiently long antisense sequence to such a regulator or modifier to provide for the blocking of expression of the target gene in the cells of interest.

3) Preparation of Tissue

The preferred tissue is primary explant or early passaged. It will be acquired using standard surgical procedures. Tissue processing for culture and/or heterotransplant will be according to established methods. Culture conditions for the disordered cells from the various aberrant program diseases or their normal counterparts are referenced in Table III. These references also provide information on acquiring and processing the appropriate cells.

Uses to provide the source material for:

a) determining the subset of the known transcriptional regulators or their direct modifiers that are expressed by a particular cell type.

b) practicing the collateral inventions; that is, diagnosis and staging an aberrant program disease or for selecting optimal treatment in clinical practice.

c) evaluating possible adverse effects of treatments for aberrant program diseases oh cultures of the three major constitutively self-renewing tissues (bone marrow, gastrointestinal epithelium, and skin). These cultures will also be used in some of the reductions to practice involving therapeutic manipulations of normal tissue. Culture conditions, Table IV.

d) The other cultures and heterotransplants to be used in the reduction to practice.

4) Discrimination of normal vs malignant cells in a mixed population.

Standard in situ hybridization procedures for detecting chromosome and/or translocation specific changes will be utilized. (Trask Trends in Genet. Z, 149, 1991).

5) Establish assays for scoring effects of manipulating transcriptional regulator function or their direct modifiers on cellular programming.

a) Aberrant program disease tissue

By definition the affected cells in these disorders express abnormal patterns of gene expression that produce the characteristic clinicopathologic features. Both of these can be monitored using established molecular and cellular techniques. The specific parameters to be assayed for each of the types of aberrant program disease given as examples are shown in Table III.

b) Normal tissue

Reprogramming normal cell behavior where the relevant programs are differentiation, proliferation and viability could serve a variety of therapeutic uses. These would include but not be limited to certain in vitro and systemic treatments: (1) expansion of normal cell numbers in vitro prior to transplantation; (2) promotion of the growth of gastrointestinal cells in the treatment of peptic ulcers and inflammatory bowel disease; (3) liver regeneration, for example, following partial destruction by a virus or toxic chemicals; (4) expansion of one or more hematopoietic cell lineages for a variety of clinical purposes including reconstitution of immune function in immunodeficiencies, counteracting the effects of agents toxic to bone marrow and in fighting infection.

All of these changes in normal cellular programming can be readily assessed using established techniques.

B) Reduction to Practice

Step 1) Determine the subset of transcriptional regulators, and their direct modifiers, expressed by the aberrantly programmed tissue, the corresponding normal tissue, and the constitutively self-renewing normal tissue. Alternatively make a similar determination for any other normal tissue that is to be therapeutically manipulated in accordance with this invention.

Step 2) Add or subtract expression of transcriptional regulator(s) or their direct modifiers from cells to be therapeutically reprogrammed and the appropriate control tissue, as previously specified.

a) Addition—Use expression vector to insert expressible gene for a particular transcriptional regulator or a direct modifier of a transcriptional regulator into aberrantly programmed cells. The inserted gene will be one that is expressed by the corresponding normal cells, but not by the aberrantly programmed cells.

b) Subtraction— i) can be achieved by the use of antisense oligonucleotides directed to the RNA of a particular transcriptional regulator or direct modulator or double-stranded oligonucleotide ligands for DNA binding domain of one or more transcriptional regulators Using prototype antisense oligonucleotide(s) or double-stranded oligonucleotides block function of specific transcriptional regulator(s) in aberrantly programmed cells or normal cells to be therapeutically manipulated through reprogramming. Alternatively use an antisense oligonucleotide directed to a direct modifier of a transcriptional regulator.

ii) Using expression vector carrying antisense DNA directed to a particular transcriptional regulator or a direct modifier of a transcriptional regulator, install the new gene in aberrantly programmed cells. The therapeutic effect will be determined in advance through the use of an antisense oligonucleotide.

Step 3) REPROGRAMMING TEST:

Using the methods and procedures described in the "Hardware for Reduction to Practice" and using the information given in Tables III and IV, perform the following functions.

a) Utilize appropriate culture conditions for normal cells to be therapeutically reprogrammed or for AP disease, the AP cells plus the corresponding normal cells and constitutively self-renewing normal tissues (gastrointestinal, bone marrow, skin);
b) For AP disease, assay one or more pathogenic features of AP cells such as those shown in Table III, according to established procedures;
c) Treat cultures with prototype agent with reprogramming potential (as oligonucleotides to TR, as oligonucleotide ligands for TR, or expression vectors).
d) Score changes in programming and choose those agents that are therapeutically useful; for example:
  1) cancer, myelodysplasiac and myeloproliferative syndrome and atherosclerosis—kill AP cells;
  2) AIDS, regenerate CD4$^+$ lymphocytes;
  3 Expand normal hematopoietic stem cells for bone marrow transplant.

Step 4) Test effect of addition or subtraction of the function of particular transcriptional regulators using the agents selected in an animal model system if the therapeutic agents are for systemic use.

Because of the need for a high degree of target homology with the corresponding human transcriptional regulator or its direct modulator the animals will of necessity nearly always be non-human primates.

In the case of evaluating agents for the treatment of aberrant program diseases the animal may either be afflicted with the disease and both the efficacy of the treatment and the side effect documented or the animal may be normal and only the side effects tested.

Step 5) Any undesirable side effects that might be produced by the potential therapeutic agents can be reduced or eliminated in several possible ways, all of which can be implemented using existing technology.

a) Antisense oligonucleotides

FIG. 1 demonstrates that there are cell type specific differences in effects of particular antisense oligonucleotides targeted to different sites on specific RNA transcripts on cell behavior. Such differences can be used to select antisense oligonucleotides that produce the desired therapeutic effects with minimal undesirable side effects.

b) Double-stranded oligonucleotide ligands

Typically more than one transcriptional regulator can bind to the same double-stranded DNA sequence, but with variable affinities. It is, therefore, possible to change the competitive inhibitor effect of such an agent relative to the potential set of target transcriptional regulators by introducing base changes. These can include mismatches. The melting temperature of the two resulting strands, however, must be $\geq 40°$ C. under physiologic conditions. The effect of such changes, therefore, can produce a more favorable therapeutic index.

Expression vectors

The levels of expression and efficiency of gene transfer can be readily adjusted on a tissue specific basis by changes in the viral envelope and/or the promoter/enhancer combination used to achieve gene expression.

Demonstration of the Reduction to Practice with a P53 Target

Step 1

It is known that p53 is expressed by primary human leukemia blast cells using the metabolic labeling technique (Smith, et al., J. Exp. Med. 164, 751, 1986.)

Step 2

A set of four different phosphorothioate antisense oligonucleotides directed to p53. RNA were prepared using an Applied Biosystems, Inc. (ABI) DNA synthesizer (Model 380B) according to the manufacturer's protocols. An antisense oligonucleotide against the HIV rev gene was used as a negative control. The sequences are set forth in the Sequence Listing hereinafter as SEQ ID NOS: 2–5. These were used to treat primary human leukemic blasts, normal human bone marrow, normal human circulating T-lymphocytes, normal adult human gastrointestinal epithelium, normal human fetal gastrointestinal epithelium and Rhesus monkey T-lymphocytes. Destruction of p53 RNA by the antisense p53 oligonucleotides was documented using PCR and/or dot blotting.

Step 3

The following effects of the antisense p53 oligonucleotides on cellular programming were evident from the results found.

1) They can irreversibly block the proliferation of, block stem cell self-renewal, or kill human cancer cells. This coupled with the lack of toxic effects on normal tissue indicates these agents can have a role in the treatment of cancer. (See Tables V–VII).
2) They promote the proliferation of gastrointestinal epithelium, indicating a role in the treatment of peptic ulcer and inflammatory bowel disease (FIG. 1). The suppressive effect of these agents on mature lymphocyte (Table IX) proliferative also supports their role in diseases such as inflammatory bowel disease that have an autoimmune component.
3) The data also demonstrates that there are cell type specific differences in responses to antisense oligonucleotides targeted to different sites on RNA transcripts of the same gene (FIG. 1). This provides a basis for optimizing therapeutic effects and for minimizing undesirable side effects.
4) These results support the general principle that antisense oligonucleotides directed to transcriptional regulator can be used to expand particular normal adult or fetal tissues vitro that could then be used for various medical purposes including transplantation (FIG. 1).
5) The cell type dependency of the effects of particular antisense oligonucleotides directed to a transcriptional regulator support the cellular program model in general and the aberrant program model in particular.

Step 4

The ability of the antisense p53 oligonucleotides to recognize the p53 RNA of Rhesus monkeys was demonstrated by showing a similar inhibitory effect on mature T-cell proliferation for both Rhesus and human cells (Table IX).

Two Rhesus monkeys weighing 8.9 kg and 6.8 kg were infused with 52.5 mg and 75.8 mg of the OL(1)p53 antisense oligonucleotide (SEQ ID NO:4) which was radiolabelled over four hours. In keeping with rodent data, tissue distribution analysis showed substantial oligonucteotide uptake compared to the levels needed to block p53 expression. Excretion studies demonstrated retention of the infused agent for more than two weeks. During this time and subsequently, the animals were extensively monitored for signs of toxicity and none were seen.
Step 5

Since no unacceptable side effects were produced in the monkeys, it has not been necessary to modify the antisense oligonucleotides.

The antisense oligonucleotide selected for practice of the invention may be any of the types described by Stein and Cohen, Cancer Research 48:2569–2668 (1988), and including without limitation, unmodified oligodeoxynucleotides, ethyl- or methyl-phosphonate modified oligodeoxynucleotides, phosphorothioate modified oligonucleotides, dithioates, as well as other oligonucleotide analogs, including those incorporating ribozyme structures, and oligoribonucleotides such as those described by Inove et al., Nucleic Acids Res. 5:6131 (1987); and Chimeric oligonucleotides that are composite RNA, DNA analogues (Inove, et al, FEBS Lett. 115:327 (1987). Oligonucleotides having a lipophilic backbone, for example, methylphosphonate analogs with ribozyme structures, may prove advantageous in certain circumstances; these molecules may have a longer half-life in vivo since the lipophilic structure may reduce the rate of renal clearance while the ribozyme structure promotes cleavage of the target RNA. Gerlach, Nature 334:585 (1988).

The oligonucleotides may be formulated into pharmaceutical compositions and administered using a therapeutic regimen compatible with the particular formulation. As described further below, with the aid of present disclosure, those of skill in the chemotherapeutic arts should be able to derive suitable dosages and schedules of administration for any of a number of suitable compositions that contain the compounds. Thus, pharmaceutical compositions within the scope of the present invention include compositions where the active ingredient is contained in an effective amount to kill the cells of the cancer without causing unacceptable toxicity for the patient. However, a preferred dosage comprises that which is sufficient to achieve an effective blood concentration of between about 1 and about 5 micromolar. Although a preferred range has been described above, determination of the effective amounts for treatment of each type of tumor may be determined by those of skill in the art of chemotherapeutic administration.

In addition to the antisense oligonucleotide compounds, the pharmaceutical compositions of the invention may contain any of a number of suitable excipients and auxiliaries which facilitate processing of the active compounds into preparations that can be used pharmaceutically. Preferably, the preparations will be designed for parenteral administration. However, compositions designed for oral or rectal administration are also considered to fall within the scope of the present invention. Preferred compositions will comprise from about 0.1 to about 1% by weight of the active ingredients.

Suitable formulations for parenteral administration include aqueous solutions of the active compounds in water-soluble or water-dispersible form. Alternatively, suspensions of the active compounds may be administered in suitable lipophilic carriers. The formulations may contain substances which increase viscosity, for example, sodium carboxymethyl cellulose, sorbitol, and/or dextran. Optionally, the formulation may also contain stabilizers. Additionally, the compounds of the present invention may also be administered encapsulated in liposomes. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

TABLE I

Analogy with Language

The following analogy with language illustrates the essential nature of the model of clinical cancer given in the patent application and the basic rationale for using antisense oligonucleotides directed against the indicated target or traitor genes as therapeutic agents. It should be clear that this is a novel, inventive and useful approach.

| RULES: | |
|---|---|
| Biology | Language Equivalent |
| The instructions for a particular pattern of gene expression (program) where key programs are differentiation, viability and proliferation | word |
| Transcriptional Regulators (or any of the other types of regulators listed as target or traitor genes | letters |
| Programmed cell death | nonsense letter combination |
| Malignant cells have different program instructions than corresponding normal cells and normal cells in general | malignant cells express unique words |
| Normal cells at different stages of differentiation express different program instructions than other cell types | different normal cell types have their own vocabulary |
| All or nearly all the letters used by malignant cells are structurally normal and appear in normal cells | the alphabet of normal malignant cell are essentially the same |
| As particular programs unfold, the pattern of regulators. expressed changes | cells express different words at different program stages |

Note: The words used in the following examples have only a loose correlation to actual cellular behaviors or programs.

| Hypothetical Example | Cell Type 1 (e.g. liver) | Cell Type 2 (e.g. kidney) |
|---|---|---|
| Normal | retard | stop |
| Low grade malignant | start | swarm |
| High grade malignant | spread | grow |
| Comments - Table I (cont.) | | |

I. ANALOGY WITH BASIC CLINICOPATHOLOGIC MECHANISMS a) "T" and "P" in normal cell type 2 but not in malignant type 1 could be considered analogous antioncogenes since they must be deleted for malignant progression. That is, for the word "stop" to be changed to the word "swarm". These deletions must occur along with the deletion of "o" and the addition of "w", "a", "r" and "m". The same letter "p", however, appears in the high grade malignant type 1 cell, while "t" appears in the low grade form. This fits the observations that antioncogenes are far from universally deleted in human cancers, that multiple genetic changes appear to be involved in carcinogenesis and that clinical cancers typically evolve phenotypically.

b) "m" and "w" could be considered analogous to "oncogenes" since they are required for "stop" evolving to "swarm" and they are not expressed in other normal adult cells. Alternatively, "m" and "w" could be normally only expressed at the embryonic-fetal stage of development.

c) "s" becomes expressed in the malignant forms of type 1 cells (ectopic expression) while it is normally expressed in type 2, but not type 1.

II. ANALOGY WITH ANTISENSE OLIGONUCLEOTIDE TREATMENT STRATEGY a) Inhibition of "t" expression will kill low grade type 1 calls but not normal cell types 1 and 2, because "start" becomes "sat" which is not a word, but "retard" and "stop" become "read" and "sop" respectively which are both words.

b) Blocking "m" but not "w" will kill malignant cell type 2 at the low grade phase since "swarm" minus "m" becomes "swar" which is not a word; but "swarm" minus "w" becomes "rams" a word.

d) Knocking out "a" will kill low grade 1 and 2 and high grade 1, but it also kills normal cell type 1. So antisense inhibition of "a" might be useful for purging bone marrow of malignant cell type 1 or 2 but not for systemic treatment.

e) Deletion of "r" would not kill normal cell type 1 ("retard" becomes "date"), but it would kill three of the four malignant cell types. The exception being low grade 1 where "start" becomes "sat".

f) Removal of "e" kills normal and high grade type 1, so it would not be expected to be a good target for systemic therapy.

g) Of the remaining letters elimination of "d" or "g" will not result in the death of any of the cell types; removal of "s" will kill high grade 1, but none of the other cell types it appears in; blocking "o" will kill both malignant forms of type 2; and inhibition of "p" will kill high grade 1 but not normal type 2.

TABLE II

Human Transcriptional Regulators

| Members | Family | Where known to be expressed | Representative Reference | Possible Direct Modifications | Reference |
|---|---|---|---|---|---|
| p 53 | — | proliferating mature T and B lymphocytes, numerous types of cancer | Kern, et al., Sci. 252 1708, 1991. | phosphorylation | Smith, et al., J. Exp. Med. 164, 751, 1986. |
| A20 | — | endothelial cells | Opipari, et al., J. Biol. Chem. 265, 14705, 1990. | — | — |
| AF-1 | — | liver | Metger, et al., J. Biol. Chem 265, 9978,1990. | — | — |
| AP-2 | — | cell lines | Comb and Goodman, Nucl. Acids Res. 18, 3975, 1990. | — | — |
| | | cell lines | Hu, et al., Genes and Dev. 4, 1741, 1990. | — | — |
| ATFI-8 | ATF | cell lines | Hoeffle,, et al., Mole. Endocrine 5. 256, 1991. | — | — |
| C/EBP | — | liver | Friedman and Muknight, Genes and Dev. 4, 1410, 1990. | — | — |
| CHF.10 | — | cell lines | Pannuti, et al., Nucl. Acids Res. 16, 4227, 1988. | — | — |
| CHF. 12 | — | cell lines | Panuti, et al., Nucl. Acids Res. 16, 4227, 1988. | | |
| CRE-BP1 | — | fetal tissue, cell lines | Maekawa, et al., EMBOJ. 8, 2023, 1989. | — | — |
| CREB | — | cell lines | Muchardt, et al., J. Virol. 64, 4296, 1990. | phosphorylation | Hoeffler, et al. Mol Endo. 5, 256, 1991. |
| E12 | — | cell lines | Mossee, et al., Cell 56, 777, 1989. | — | — |
| E47 | — | cell lines | Mosse, et al., Cell 56, 777, 1989. | — | — |
| E2A | | all blasts | Kamps, et al., 60, 535, 1990. | — | — |
| EBP1 | — | cell lines | Clark, et al., Genes Dev. 2, 991, 1988. | — | — |
| EGR 1-3 | EGR | cell lines, PMA induced mononuclear cells | Rangneka,, et al., Nucl. Acids Res. 18 2749, 1990. | — | — |
| EGR 1,2 | ETS | cell lines | Watson, et al., PNAS 85, 7862, 1988. | — | — |
| ETS 1,2 | ETS | T lymphocytes, fetal liver, astocytes | Bhat, et al., PNAS 97 3723, 1990. | | |
| GLI-1-3 | GLI | embryonal carcinoma, myometrium testis, placenta | Ruppert, et al., Mol. Cell. Biol. 8, 3104, 1988. | — | — |
| HKR1-4 | HKR | testis, placenta, kidney, colon, lung, brain, embryonal | Ruppert, et al., Mol. Cell. Biol. 8, 3104, 1988. | — | — |

TABLE II-continued

Human Transcriptional Regulators

| Members | Family | Where known to be expressed | Representative Reference | Possible Direct Modifications | Reference |
|---|---|---|---|---|---|
| HOX 1.4, 2.1, 2.2, 2.3, 2.4, 2.5, 2.6, 2.7, 2.8, 2.9, 5.1, 5.2, 5.4. 6.1, 6.2, 7 | homeobox | carcinoma cell lines, embryo | | | |
| HPFp1-9 | HPF$_p$ | placenta | Bellefroid, et al., DNA 8, 377, 1989. | — | — |
| H-plk | — | placenta | Kato, et al., Mol. Cell. Biol. 10, 4401, 1990. | — | — |
| HS1 | — | lymphocytes | Kitamura, et al., Nucl. Acids Res. 17, 93167, 1989. | — | — |
| hXBP | — | lymphocytes | Liou, et al., Sci. 247 1581, 1990. | — | — |
| I$_K$B | — | placenta | Zabel and Baeuele, Cell 61, 255, 1990. | — | — |
| ISGFI-3 | — | cell lines | Pine, et al., Mol. Cell. Biol. 10, 2448, 1990. | — | — |
| JUNB | JUN | cell lines | Nomura, et al., Nucle. Acids Res. 18, 3047, 1990. | — | — |
| C-JUN | JUN | cell lines | Nomura, et al., Nucle. Acids Res. .18, 3047, 1990. | — | — |
| JUN-D | JUN | cell lines | Nomura, et al., Nucle. Acid, Res. 18, 3047, 1990. | — | — |
| K8 | homeobox | cell lines | Kongsuwan, et al., ENMOJ. 7, 2131, 1988. | — | — |
| lyl-1 | — | cell lines | Mellentin, et al., Cell 58, 77, 1989. | — | — |
| MAX | — | cell lines | Blackwood and Eisenman Sci. 251, 1211, 1991. | — | — |
| MBP-1 | — | cell lines | Baldwin, et al., Mol. Cell. Biol. 10, 1406, 1990. | — | — |
| A-myb | myb | cell lines | Normora, et al., Nucl. Acids Res. 16, 11075, 1988. | — | — |
| B-myb | myb | cell lines | Normora, et al., Nucl. Acids Res. 16, 11075, 1988. | — | — |
| C-myb | myb | cell lines, hematopoietic tissue | Normora et al., Nucl. Acids, Res. 16, 11075, 1988. | — | — |
| C-myc | myc | cell lines, hematopoietic tissue | Gazin, et al., ENBOJ. 3, 383, 1984. | — | — |
| L-myc | myc | placenta, lung cancer | Kaye, et al., Mol. Cell. Biol. 8, 186, 1988. | — | — |
| N-myc | myc | neuroblastoma | Slaman, et al., Sci. 232, 768, 1986. | — | — |
| myf5 | — | muscle | Braun, et al., Nature 346, 663, 1990. | — | — |
| NF-E1,2 | NF-E | hematopoietic cells | Mignotte, et al., Nucl. Acids Res. 17, 37, 1989. | — | — |
| NFE6 | NF-E | hematopoietic cells | Colin, et I., J. Biol. Chem. 265, 16729, 1990. | — | — |
| NF-µE1 | — | lymphocytes | Sen and Saitimore, Cell 46, 705, 1986. | — | — |
| NF-µE3 | — | lymphocytes | Sen and Saltimore, Cell 46, 705, 1986. | — | — |
| NFGMa | — | embryonic tissue, hematopoietic cells | Shannon, et al., Mol. Cell. Biol. 10, 2950, 1990. | — | — |
| NFGMb | — | hematopoietic cells | Shannon, et al., Mol. Cell. Biol. 10, 2950, | | |

TABLE II-continued

Human Transcriptional Regulators

| Members | Family | Where known to be expressed | Representative Reference | Possible Direct Modifications | Reference |
|---|---|---|---|---|---|
| NF-IL6 | — | monocytes | Akira, et al., EMBOJ. 2, 1897, 1990. | — | — |
| NF-$_\kappa$B | — | lymphocytes, cell lines | Ruben, et al., Sci. 251, 1490, 1991. | — | — |
| NF-5 | — | lymphocytes | Kobr, et al., Mol. Cell. Biol. 10, 965, 1990. | — | — |
| 225 | — | cell lines, lymphocytes | Wright, et al., Sci. 248, 588, 1990. | — | — |
| 243 | — | lymphocytes | Bours, et al., Nature 348, 76, 1990. | — | — |
| Oct 1 | Oct | cell lines | Johnson, et al., Mol. Cell. Biol. 10, 1982, 1990. | — | — |
| Oct 2 | Oct | cell lines | Johnson, et al., Mol. Cell. Biol. 10, 1982, 1990. | — | — |
| Oct 3 | Oct | embryonic | Scholer, et al., EMBOJ. 9, 2185, 1990 (murine) | — | — |
| Pit-1 | — | pituitary | Chen, et al., Nat., 346, 583, 1990. | — | — |
| PL1 | homeobox | cell lines | Shen, et al., PNAS 86, 8536, 1989. | — | — |
| Pr1 | homeobox | cell lines | Kemps, et al., Cell 60, 547, 1990. | — | — |
| Rb | — | hematopoietic cells, retinal cells | Lee, et al., Sci. 235, 1394, 1987. | phosphorylation | Yen, et al., Exp. Cell. Res. 192, 289, 1991. |
| RF-y | — | cell lines | Reith, et al., Cell 53 897, 1988. | — | — |
| RF-x | — | lymphocytes | Reith, et al., Genes Dev. 4, 1528, 1990. | — | — |
| Rhombotin | — | cell lines | McGuire, et al., Mol. Cell. Biol. 9, 2124, 1989. | — | — |
| SCL | — | fetal liver, hematopoietic cells, placenta | Beyley, et al., PNAS 86, 10128, 1989. | — | — |
| Sp-1 | — | cell lines | Pugh and Tjian, Cell 61, 1187, 1990. | — | — |
| SRF | — | cell lines | Norman, et al., Cell 55, 989, 1988. | — | — |
| Tal | — | cell lines | Chen, et al., ENBOJ. 2, 415, 1990. | — | — |
| TCF-1 | — | lymphocytes | Van de Watering, et al., EMBOJ. 10, 123, 1991. | — | — |
| TFE3 | — | lymphocytes | Beckmann, et al., Genes Dev. 4, 167, 1990. | — | — |
| VAu | — | hematopoietic cells | Katzav, et al., EMBOJ. 8, 2283, 1989. | — | — |
| cfos | fos | hematopoietic cells | Runkel, et al., Mol. Cell. Biol. 11, 1270, 1991. | phosphorylation | Barber and Verma, Mol. Cell. Biol. 7 2201 1997, |
| fos-B | fos | cell lines | Mumberg et al, Genes Dev, 5, 1212, 1991 | — | — |
| fra-2 | fos | cell lines PNAS, 87, 3614, 1990 (chicken) | Nishina et al, | — | — |
| glucocorticoid receptor | steroid receptor super family | lymphocytes and numerous other cell types | O'Malley, Mole Endocrin., 4, 363, 1990 | — | — |
| androgen receptor | steroid receptor super family | male reproductive organs, muscle | O'Malley, Mole Endocrin., 4, 363, 1990 | — | — |
| progesterone receptor | steroid receptor super family | female reproductive organs | O'Malley, Mole Endocrin., 4, 363, 1990 | — | — |
| estrogen receptor | steroid receptor super family | female reproductive organs | O'Malley, Mole Endocrin., 4, 363, 1990 | — | — |

TABLE II-continued

Human Transcriptional Regulators

| Members | Family | Where known to be expressed | Representative Reference | Possible Direct Modifications | Reference |
|---|---|---|---|---|---|
| estrogen related receptors | steroid receptor super family | female reproductive organs | O'Malley, Mole Endocrin., 4, 363, 1990 | — | — |
| retinoic acid receptor | steroid receptor super family | hematopoietic cells, epithelial tissue | O'Malley, Mole Endocrin., 4, 363, 1990 | — | — |
| thyroid hormone receptor | steroid receptor super family | numerous tissues | O'Malley, Mole Endocrin., 363, 1990 | — | — |
| vitamin D receptor | steroid receptor super family | hematopoietic and many other cell types | O'Malley, Mole Endocrin., 4, 363, 1990 | — | — |
| mineralocorti-coid receptor | steroid receptor super family | kidney, colon, salivary glands | O'Malley, Mole Endocrin., 4, 363, 1990 | — | — |
| MZF-1 | Kruppel zinc finger like family | CML, placenta | Hromas, et al., J. Biol. Chem. 266, 14183, 1991 | — | — |
| HB9 | homeobox | hematopoietic, fetal | Deguchi and Kehrl, Blood 78, 323, 1991 | — | — |
| HB24 | homeobox | hematopoietic, fetal | Deguchi and Kehrl, Blood 78, 323, 1991 | — | — |
| vHNF1 | homeobox | liver | Bach, et al., Nucl. Acids Res. 19, 3553, 1991 | — | — |
| HOX11 | homeobox | liver, some T cell leukemias | Hatano, et al., Sci. 253, 79, 1991 | — | — |
| PL2 | homeobox | cell lines | Lowney, et al., Nucl. Acids Res. 19, 3443, 1991 | — | — |
| rel | | cell lines | Brownell, et al., Mol. Cell Biol. 5, 2826, 1985 | — | — |
| HSF | | many cell types | Cunniff, et al., Mol. Cell Biol. 11, 3504, 1991 | — | — |
| NF-AB | | cell lines | Won and Baumann, Mol. Cell Biol. 11, 3001, 1991 | — | — |
| CCG1 | | cell lines | Sekiguchi, et al., Mol. Cell Biol. 11, 3317, 1991 | phosphorylated | Sekiguchi, et al., Mol. Cell. Biol., 11, 3317, 1991 |
| rhom-2 | rhombotin | cell lines, embryonic tissue | Buehm, et al., PNAS 88, 4367, 1991 | — | — |
| rhom-3 | rhombotin | cell lines | Buehm, et al., PNAS 88, 4367, 1991 | — | — |
| GATA-3 | | T cells | Ho, et al., ENSO J. 10, 1187, 1991 | — | — |
| IP-1 | | cell lines | Auwerx and Sassone-Corsi, Cell 64, 983, 1991 | phosphorylated | Auwerx and Sassone-Corsi, Cell 64, 983, 1991 |

TABLE III

| Disease | Cell Type | Representative Culture References | Pathological Features of Aberrant Programming | Pathologic Change Reference |
|---|---|---|---|---|
| Cancer | A) Hematopoietic | A-1) Eaves, et al., J. Tiss. Cult. Meth. 13, 55, 1991. A-2) Messner, et al Blood 70, 1425, 1987. A-3) Uckin and Heerema Leuk. Lymph. 2, 1, 1990. A4) Caligaris-Cappio, et al., Blood 77, 2688, | 1) inappropriate proliferation 2) ability to survive in inappropriate sites in body 3) inappropriately invasive | 1–3) Kissane (ed) Anderson's Radiology C. V. Mosby St. Louis, 9th ed. 1990. |

TABLE III-continued

| Disease | Cell Type | Representative Culture References | Pathological Features of Aberrant Programming | Pathologic Change Reference |
|---|---|---|---|---|
| | B) Solid Tissue | 1991. A-5) Hog and McCulloch, Blood 66, 748, 1985. B-1) Moyer, 1. Tiss. Cult. Meth. 8, 63. 1983. B-2) Moyer and Poste (eds.), Colon Cancer Cells, Academic Press, San Diego, CA 1990. (Dr. Moyers' culture system works for most primary human sarcomas and carcinomas) | | |
| Myelodysplasia | hematopoietic | a) Firken, et al., Br. J. Haemat. 75, 476, 1990. b) Aoki, et al., Amer. J. Hemat. 35, 6, 1990. c) Nagler, et al., Blood 76, 1299, 1990. | 1) impairment of blood cell differentiation as judged by standard clinical diagnostics 2) Unpaired colony formation by multi-potential progenitors 3) immune abnormalities including (a) deficits in CD4+ lymphocytes and (b) deceased NK cells 4) apoptosis 4c) suppressed clonal expansion of myeloid progenitors from patient, but not normal in presence of patient serum | 1–3)List,et al., J Clin. Oncol. 1424, 1990. 4) Clark and Lampert, Leuk. Lymph. 2, 415, 1990. 4c) Donohue, et al., Nature 326, 200, 1982. |
| Myeloproliferative Disorders | hematopoietic | a) Eaves, et al., J. Tiss. Cult. Meth. 13, 55, 1991. b) Messner, et al., Blood 70, 1425, 1987. c) Fauser and Messner, Blood 58, 1224, 1981. | inappropriate clonal prolifertion of particular blood cell lineages | Adamson and Fialkon, Br. J. Haemat. 38, 299, 1978. |
| ARC/ AIDS | hematpoietic | Current protocols in immunology Coligan, et al. (eds.), John Wiley, Inc., N.Y. 1991 | 1) reduction in CD4+ lymphocytes and an inversion of the CD4+ to CD8+ 2) reduction in CD16$^{30}$ CD8+CD3- cells 3) functional defects in lypho-cytes including: (a) altered responses to certain antigens and mitogens; (b) defect in ability to under-go clonal expansion; (c) abnormalities in IL-2 receptor expression 4) functional defects in other blood cells (a) abnormal TNF production; (b) defective platelet production | 1) Faut Sci. 239, 617, 1988. 2) Ma.,r. et al., AIDS Res. Human Retro. f, 1451, 1990. 3a) Pinching and Nye, Immunol. Today 11, 256, 1990. 3a) Allouche, et al., Clin. Exp. Imm. 200, 1990. 3b) Pantaleo, et al., J. Immunol. 144, 1696, 1990. 3c) Prince, et al., Clin. Exp. Immun. 67, 59, 1987. 4a) Oteh, J. Int. Med. 228, 549, 1990. 4b) Zucker-Franklin and Cao, PNAS 86 5595, 1989. |
| Atherosclerosis | smooth muscle | a) Orekhov, et al., Atherosclerosis 60, 101, 1986. b) Campbell and Campbell, | Shift from contractile to synthetic phenotype. Features of later include: 1) proliferation | 1) Oisson (ed) Atherosciersosis: Biology and Clinical Science, Churcher Livingstone, NY 1997. |

TABLE III-continued

| Disease | Cell Type | Representative Culture References | Pathological Features of Aberrant Programming | Pathologic Change Reference |
|---|---|---|---|---|
| | | Vascular Smooth Muscle in Culture, Vols. I and II, CRC Press, Boca Raton, FL, 1987 | 2) increase HLA-DR expression<br>3) loss of muscle protein<br>4) growth factor production<br>5) sythesis of extracellular matrix<br>6) production of decay accelerating factor<br>7) shift from media to initial location | 2) Jonasson, et al., J. Clin. Invest. 76, 125, 1985.<br>3) Glukhova, et al., PNAS 85, 9542, 1988.<br>4) Wilcox, et al., J. Clin. Invest. 82, 1134, 1988.<br>5) Mosse, et al., Lab. Invest. 53, 556, 1985.<br>6) Seifert and Hansson, J. Clin. Invest. 84, 597, 1989.<br>7) Betz, et al., J. Cell. Phys. 147, 385, 1991. |

TABLE IV

Representative Tissue Culture References for Primary Normal Human Tissue

| Tissue | Reference |
|---|---|
| Gasterointestinal (and a variety of other epithelial and mesenchymal cell | a) Moyer and Gendelman, J. Leuk. Biol. 49, 499, 1991.<br>b) Moyer, J. Tiss. Cult. Meth. 13, 107, 1991. |
| bone marrow | Eaves, et al., J. Tissue Cult. Meth. 13, 55, 1991. |
| hematopoietic stem cells | a) Messner, et al., Blood, 70, 1425, 1987.<br>b) Bernstein, et al., Blood 77, 2316, 1991.<br>c) Caux, et al., Blood 75, 2292, 1990. |
| liver | Gomez-Lechan, et al., In Vitro Cell. Dev. Biol. 26, 67, 1990. |

TABLE V

Effect of p53 a.s. ODNs on in vitro growth of partially purified blasts from peripheral blood of patients with acute non-lyliphocytic leukemia. Values represent triplicate cultures from seven separate experiments, a through g, including six different patients at either presentation or relapse. Peripheral blood leukemia blasts were isolated by Ficoll-Hypaque separation and sheep erythrocyte T-cell resetting. Cells were plated at $5 \times 10^5$/ml in medium as described (*). Control cultures either contained no a.s. ODNs (control), or a.s. ODN to rev (HIV). A.s. ODNs were added 24 hours after plating. In A., aliquots were removed from culture on days 5, 10 and 15 and counted for Trypan blue exclusion. In B., cells were removed on day 10 washed to remove a.s. ODN, replated at $5 \times 10^5$/ml and counted 5 days later (day 15). nd = not done.

A. percent viable cells of control

| | a | | | b | | |
|---|---|---|---|---|---|---|
| | day | | | | | |
| a.s. ODN | 5 | 10 | 15 | 5 | 10 | 15 |
| Control | 100 | 100 | 100 | 100 | 100 | 100 |
| HIV | nd | nd | nd | 54 | 55 | 75 |
| OL(1) | 88 | 4 | 1 | 0 | 0 | 0 |
| A(1) | 51 | 74 | nd | 0 | 0 | 0 |
| A(3) | 101 | 15 | 13 | 51 | 18 | 21 |
| C(1) | 60 | 57 | 41 | nd | nd | nd |

| | c | | | d | | |
|---|---|---|---|---|---|---|
| | 5 | 10 | 15 | 5 | 10 | 15 |
| | 100 | 100 | nd | 100 | 100 | 100 |
| | 46 | 45 | nd | 100 | 79 | 89 |
| | 22 | 4 | nd | 64 | 21 | 27 |
| | 86 | 21 | nd | 64 | 43 | 29 |
| | 30 | 2 | nd | 41 | 24 | 24 |
| | 49 | 15 | nd | 55 | 19 | 17 |

B. percent of control

| | e Replated | | | f Replated | | | g Replated | | |
|---|---|---|---|---|---|---|---|---|---|
| a.s. | day | | | | | | | | |
| ODN | 5 | 10 | 15 | 5 | 10 | 15 | 5 | 10 | 15 |
| Control | 100 | 100 | 100 | 100 | 100 | 100 | 100 | 100 | 100 |
| HIV | 102 | 95 | 103 | 83 | 103 | 92 | 90 | 97 | 91 |
| OL(1) | 68 | 48 | 33 | 45 | 44 | 31 | 45 | 34 | 43 |
| A(1) | 77 | 46 | 37 | 53 | 44 | 71 | 59 | 75 | 64 |
| A(3) | 93 | 55 | 37 | 51 | 57 | 73 | 63 | 51 | 62 |
| C(1) | 72 | 49 | 41 | 53 | 59 | 37 | 66 | 63 | 77 |

*Buick, et al., Blood 54, 95, 1979.

TABLE VI

Effect of p53 a.s. ODNs on in vitro colony formation (CFU-L) of cells removed on either day 0 or 7 of the two of the cultures described in Table V (f and g). Values represent mean ± SD of triplicate cultures. Controls were as described in Table V. Cells were cultured according to B. Lange (*) at 1 × 10$^5$/ml. A fraction of the cells from day 7 colonies were washed and replated at 1 × 10$^5$/ml as described (*) in the absence of a.s. ODN. A colony was defined as >20 cells; day 7 control colonies varied from 70 to 240, day 14 colonies varied from 13 to 55. n.d. = not done.

|  | f replated | | g replated | |
|---|---|---|---|---|
|  | day | | | |
| a.s. ODN | 7 | 14 | 7 | 14 |
| Control | 100 | 100 | 100 | 100 |
| HIV | 87 | 92 | 98 | 82 |
| OL(1) | 17 | 15 | 60 | 2 |
| A(1) | 28 | 138 | 79 | 262 |
| A(3) | 58 | 108 | 96 | 24 |
| C(1) | 23 | 8 | 81 | 4 |

*Lange, et al., Blood 70, 192, 1982.

TABLE VII

Effect of p53 a.s. ODN on in vitro growth of normal bone marrow. Values represent the cumulative mean ± SD of triplicate cultures from three separate experiments. Mononuclear cells were isolated by Ficoll-Hypaque separation. Cells were plated at 2 × 10$^6$/ml in medium as described (*) except for substituting horse for human serum. Control cultures either contained no a.s. ODN, or a.s. ODN to rev (HIV). A.s. ODNs were added 24 hours after plating. Aliquots were removed from culture on days 5 and 10, and counted for Trypan blue exclusion.

|  | Viable cells × 10$^5$ | |
|---|---|---|
| a.s. ODN | day 5 | 10 |
| Control | 12.7 ± 3.3 | 13.1 ± 2.5 |
| HIV | 11.8 ± 2.6 | 11.5 ± 2.2 |
| OL(1) | 12.1 ± 2.6 | 12.0 ± 1.8 |
| A(1) | 11.9 ± 2.1 | 12.2 ± 1.5 |
| A(3) | 12.1 ± 2.7 | 14.5 ± 1.4 |
| C(1) | 9.7 ± 2.0 | 10.9 ± 0.5 |

*Bayever, et al., Exp. Cell Rev. 179, 168, 1988.

TABLE VIII

Effect of p53 a.s. ODNs on in vitro colony formation of hematopoietic progenitors removed on day 7 from three of the normal bone marrow cultures described in Table VI. Values represent the cumulative mean ± SD of triplicate cultures. Controls were as described in Table V. Cells were cultured as described (*), except they were plated at 1 × 10$^5$/ml. A fraction of the cells from day 7 colonies were washed and replated at 5 × 10$^4$/ml for the CFU-Mix and BFU-E, or 1 × 10$^5$/ml for the CFU-GM as described (*). A colony was defined as >20 cells. All colonies were cultured in the absence of a.s. ODNs.

| a.s. ODN | CFU-Mix | BFU-E | CFU-GM |
|---|---|---|---|
| Control | 3.9 ± 4.5 | 4.4 ± 7.2 | 237.6 ± 100.1 |
| HIV | 1.1 ± 0.9 | 1.0 ± 1.0 | 329.1 ± 161.9 |
| OL(1) | 1.8 ± 1.8 | 15.8 ± 1.8 | 278.9 ± 117.9 |
| A(1) | 9.5 ± 6.7 | 11.6 ± 7.8 | 330.3 ± 123.8 |
| A(3) | 1.0 ± 1.0 | 1.3 ± 1.8 | 261.3 ± 90.2 |
| C(1) | 3.4 ± 4.1 | 1.0 ± 1.9 | 254.5 ± 94.9 |

*Messner, et al., Blood 70, 1425, 1987. Caux, et al., Blood 75, 2292, 1990.

TABLE IX

Method for non-human primate peripheral blood T-cell studies:
1. Heparinized blood was diluted by one third with HBSS, layered over Ficoll-Hypaque and centrifuged at 1600 r.p.m., for 40 minutes at 20° C.
2. Interface mononuclear cells were recovered and washed twice with HBSS, resuspended in RPMI 1640 with 10% FCS to $1 \times 10^6$/ml in the presence of PHA (10 µg/ml).
3. Cells were incubated at 37° C. in 5% $CO_2$ for 72 to 96 hours.
4. Cells were harvested, washed and replated at $5 \times 10^5$/ml in medium consisting of RPMI 1640 with 10% FCS and 10% IL-2.
5. After a 24 hour incubation the a.s. ODN was added to the culture at a 10 µM concentration.
6. At 2 to 3 day intervals an aliquot was removed and counted for Trypan blue exclusion.

|  | Media | A(1) | Oh(1) | A(3) | C(1) | HIV-2 |
|---|---|---|---|---|---|---|
| BMC039 - PHA-primed human T-cells PHA stimulated → Day 4 wash + place in IL-2 = "Day 0", "Day 1" add 10 µM oligo ||||||  |
| Day 0 | $2 \times 10^5$/ml | $2 \times 10^5$/ml | $2 \times 10^5$/ml | $2 \times 10^5$/ml | $2 \times 10^5$/ml | $2 \times 10^5$/ml |
| Day 2 | $8 \times 10^5$ | 3.6 | 5 | 4.2 | 4.2 | 6.8 |
|  | 8.2 | 4.4 | 5.2 | 5 | 5 | 7.4 |
|  | 7.4 | 3.8 | 4 | 4 | 5.2 | 8.6 |
|  | $7.9 \times 10^5$ | $3.9 \times 10^5$ | $4.7 \times 10^5$ | $4.4 \times 10^5$ | $4.8 \times 10^5$ | $7.6 \times 10^5$ |
| Day 4 | $11.2 \times 10^5$ | 7.2 | 5.6 | 4 | 9.2 | 10.6 |
|  | 11.4 | 6.6 | 8 | 6 | 8.6 | 10.4 |
|  | 10.6 | 8 | 6.2 | 7.2 | 7.8 | 10 |
|  | $11.1 \times 10^5$ | $7.3 \times 10^5$ | $6.6 \times 10^5$ | $5.7 \times 10^5$ | $8.5 \times 10^5$ | $10.3 \times 10^5$ |
| Day 7 | $18.2 \times 10^5$ | 7 | 8.8 | 13 | 9.2 | 15.4 |
|  | 19.6 | 7.4 | 6.6 | 10.4 | 10.8 | 14.2 |
|  | 18.8 | 8.2 | 9.8 | 11.2 | 11.6 | 14.6 |
|  | $18.9 \times 10^5$ | $7.5 \times 10^5$ | $8.4 \times 10^5$ | $11.5 \times 10^5$ | $10.5 \times 10^5$ | $14.7 \times 10^5$ |
| On "Day 4" cells were removed, washed free of oligo and replated at $2 \times 10^5$ml. Replated cells → single cells → * (Day 4 = $2 \times 10^5$/each) ||||||  |
| Day 7 | $6.3 \times 10^5$ | 6.6 | 6.5 | 6.1 | 6.5 | 6.1 |
| Day 9 | $7.1 \times 10^5$ | 6.8 | 6.8 | 6.9 | 6.9 | 6.7 |
| BMC028 - 2 samples of monkey PB PHA prime → onto IL-2, then oligo ||||||  |
| Day 0 | $2 \times 10^5$/ml | $2 \times 10^5$/ml | $2 \times 10^5$/ml | $2 \times 10^5$/ml | $2 \times 10^5$/ml | $2 \times 10^5$/ml |
| Day 1 | 10 µM oligo | 10 µM oligo | 10 µM oligo | 10 µM oligo | 10 µM oligo | 10 µM oligo |
| Day 4 Primate A |  |  |  |  |  |  |
|  | $1.0 \times 10^5$ | 0.6 | 0.47 | 0.33 | 0.53 | 1.2 |
|  | 1.13 | 0.47 | 0.47 | 0.27 | 0.4 | 1.0 |
|  | $1.07 \times 10^5$ | $0.53 \times 10^5$ | $0.47 \times 10^5$ | $0.3 \times 10^5$ | $0.47 \times 10^5$ | $1.1 \times 10^5$ |
| Primate B |  |  |  |  |  |  |
|  | $1.93 \times 10^5$ | 1.67 | 0.67 | 0.73 | 0.53 | $1.6 \times 10^5$ |
| Day 6 Primate A |  |  |  |  |  |  |
|  | $2.0 \times 10^5$ | 1.4 | 1.07 | 1.33 | 1.4 | 3.2 |
|  | 2.93 | 1.2 | 1.33 | 1.07 | 1.2 | 2.67 |
|  | $2.47 \times 10^5$ | $1.33 \times 10^5$ | $1.2 \times 10^5$ | $1.2 \times 10^5$ | $1.33 \times 10^5$ | $2.93 \times 10^5$ |
| Primate B |  |  |  |  |  |  |
|  | $2.2 \times 10^5$ | $1.2 \times 10^5$ | $0.7 \times 10^5$ | $1 \times 10^5$ | $0.8 \times 10^5$ | $2.3 \times 10^5$ |
| Day 8 bacteria in A Primate B |  |  |  |  |  |  |
|  | $2.9 \times 10^5$ | $1 \times 10^5$ | $0.4 \times 10^5$ | $0.7 \times 10^5$ | $1.2 \times 10^5$ | $2.4 \times 10^5$ |
| Day 10 bacteria emerging in B |  |  |  |  |  |  |

While the present invention has been described in conjunction with a preferred embodiment and specific examples, the description is not meant to limit it. One of ordinary skill, with the aid of the present disclosure, may be able to effect various changes, substitutions of equivalents and other alterations to the methods and compositions set forth. Therefore, the protection granted by Letters Patent should not be limited except by the language of the claims as set forth below.

What is claimed is:

1. An oligonucleotide, selected from the group consisting of:

5'-ATCTGACTGC GGCTCCTCCA-3' (Sequence I.D. No. 2)

5'-GACAGCATCA AATCATCCAT-3' (Sequence I.D. No. 3)

5'-CCCTGCTCCC CCCTGGCTCC-3' (Sequence I.D. No. 4)

5'-AGTCTTGAGC ACATGGGAGG-3' (Sequence I.D. No. 5).

2. The oligodeotide of claim 1 wherein the melting point is equal to or greater than 40° C.

3. A modified oligonucleotide as claimed in claim 1, having a modification selected from the group consisting of phosphorothioate modification, dithioate modification, methylphosphonate modification and ethylphosphonate modification.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( i i i ) HYPOTHETICAL: NO ( i v ) ANTI-SENSE: YES ( x i ) SEQUENCE DESCRIPTION: SEQ ID NO:1:

TCTCTCCGCT TCTTCCTGCC    20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( i i i ) HYPOTHETICAL: NO ( i v ) ANTI-SENSE: YES ( x i ) SEQUENCE DESCRIPTION: SEQ ID NO:2:

ATCTGACTGC GGCTCCTCCA    20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( i i i ) HYPOTHETICAL: NO ( i v ) ANTI-SENSE: YES ( x i ) SEQUENCE DESCRIPTION: SEQ ID NO:3:

GACAGCATCA AATCATCCAT    20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( i i i ) HYPOTHETICAL: NO (iv) ANTI-SENSE: YES (xi) SEQUENCE DESCRIPTION: SEQ ID NO:4:

CCCTGCTCCC CCCTGGCTCC 20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (iv) ANTI-SENSE: YES (xi) SEQUENCE DESCRIPTION: SEQ ID NO:5:

AGTCTTGAGC ACATGGGAGG 20